(12) United States Patent
Xie et al.

(10) Patent No.: US 12,357,898 B2
(45) Date of Patent: Jul. 15, 2025

(54) MULTIMODAL HUMAN-ROBOT INTERACTION SYSTEM FOR COMPENSATION MOVEMENT OF HEMIPLEGIC UPPER LIMB

(71) Applicant: SOUTH CHINA UNIVERSITY OF TECHNOLOGY, Guangdong (CN)

(72) Inventors: Longhan Xie, Guangdong (CN); Siqi Cai, Guangdong (CN); Shuangyuan Huang, Guangdong (CN); Guofeng Li, Guangdong (CN)

(73) Assignee: SOUTH CHINA UNIVERSITY OF TECHNOLOGY, Guangdong (CN)

( * ) Notice: Subject to any disclaimer, the term of this patent is extended or adjusted under 35 U.S.C. 154(b) by 1036 days.

(21) Appl. No.: 17/422,757

(22) PCT Filed: Oct. 31, 2019

(86) PCT No.: PCT/CN2019/114914
§ 371 (c)(1),
(2) Date: Jul. 14, 2021

(87) PCT Pub. No.: WO2020/199578
PCT Pub. Date: Oct. 8, 2020

(65) Prior Publication Data
US 2022/0126189 A1 Apr. 28, 2022

(30) Foreign Application Priority Data
Apr. 4, 2019 (CN) .......................... 201910272804.X

(51) Int. Cl.
*G16H 20/30* (2018.01)
*A61H 1/02* (2006.01)
(Continued)

(52) U.S. Cl.
CPC ....... *A63B 71/0622* (2013.01); *A61H 1/0274* (2013.01); *A61H 1/0277* (2013.01);
(Continued)

(58) Field of Classification Search
CPC .. A61H 1/0277; A61H 1/0274; A61H 1/0281; A61H 1/0285; A61H 1/0288;
(Continued)

(56) References Cited

U.S. PATENT DOCUMENTS

2006/0293617 A1* 12/2006 Einav ............... A63B 23/03541
601/5
2008/0288107 A1* 11/2008 Tokita .................. G09B 19/003
901/50

(Continued)

FOREIGN PATENT DOCUMENTS

| CN | 103230664 | 8/2013 |
|---|---|---|
| CN | 203829250 | 9/2014 |

(Continued)

OTHER PUBLICATIONS

"International Search Report (Form PCT/ISA/210) of PCT/CN2019/114914," mailed on Feb. 3, 2020, with English translation thereof, pp. 1-6.

(Continued)

*Primary Examiner* — Rachel T Sippel
*Assistant Examiner* — Gwynneth L Howell
(74) *Attorney, Agent, or Firm* — JCIPRNET

(57) ABSTRACT

A multimodal human-robot interaction system for compensation movement of a hemiplegic upper limb includes a compensation monitoring module, a compensation evaluation module and a compensation reducing module. The compensation reducing module includes a robot and a virtual reality system. The robot assists the hemiplegic upper limb in performing rehabilitation training, and adjusts a (Continued)

training action according to a compensation monitoring result and evaluation of compensation to realize passive reducing of compensation movement of the hemiplegic upper limb. The compensation monitoring module acquires data during a rehabilitation therapy. The compensation evaluation module processes and analyzes comprehensive data of the hemiplegic upper limb to obtain the evaluation of compensation. The virtual reality system displays a rehabilitation training scene, a real-time movement posture of the hemiplegic upper limb and the evaluation of compensation and instructs a patient to reduce the compensation movement using visual display and voice feedback.

8 Claims, 1 Drawing Sheet

(51) Int. Cl.
 *A63B 71/06* (2006.01)
 *G06F 3/01* (2006.01)
(52) U.S. Cl.
 CPC ......... *A61H 1/0281* (2013.01); *G16H 20/30* (2018.01); *A61H 2201/1659* (2013.01); *A61H 2201/5043* (2013.01); *A61H 2201/5048* (2013.01); *A61H 2230/085* (2013.01); *A63B 2071/063* (2013.01); *A63B 2071/0647* (2013.01); *G06F 3/011* (2013.01)
(58) Field of Classification Search
 CPC ........ G16H 20/30; A63B 24/00; A63B 71/00; A63B 71/0622; A61B 5/389
 See application file for complete search history.

(56) References Cited

U.S. PATENT DOCUMENTS

| | | | |
|---|---|---|---|
| 2011/0004322 A1* | 1/2011 | Sankai | A61H 3/008 623/25 |
| 2011/0112441 A1* | 5/2011 | Burdea | A63B 24/0021 600/595 |
| 2017/0209737 A1* | 7/2017 | Tadi | A61B 5/0036 |
| 2019/0269343 A1* | 9/2019 | Ramos Murguialday | A61B 5/1107 |
| 2019/0384391 A1* | 12/2019 | Li | G06F 3/011 |
| 2020/0346347 A1* | 11/2020 | Sankai | B25J 13/082 |
| 2021/0106453 A1* | 4/2021 | Goel | A63B 23/1245 |

FOREIGN PATENT DOCUMENTS

| | | |
|---|---|---|
| CN | 104173124 | 12/2014 |
| CN | 107320285 | 11/2017 |
| CN | 108154912 | 6/2018 |
| CN | 109243572 | 1/2019 |
| CN | 110123572 | 8/2019 |
| JP | H09248322 | 9/1997 |

OTHER PUBLICATIONS

Chengliang Li et al., "The virtual training method of upper extremities with the supporting of recognition of compensative motor", Chinese Journal of Rehabilitation Medicine, vol. 27, Issue 8, Aug. 2012, with English abstract, pp. 732-737.
Chongyang Yao et al., "Research on compensatory movement of robot assisted upper limb rehabilitation training", Chinese Journal of Rehabilitation Medicine, vol. 25, No. 11, Nov. 2010, with English abstract, pp. 1085-1089.

* cited by examiner

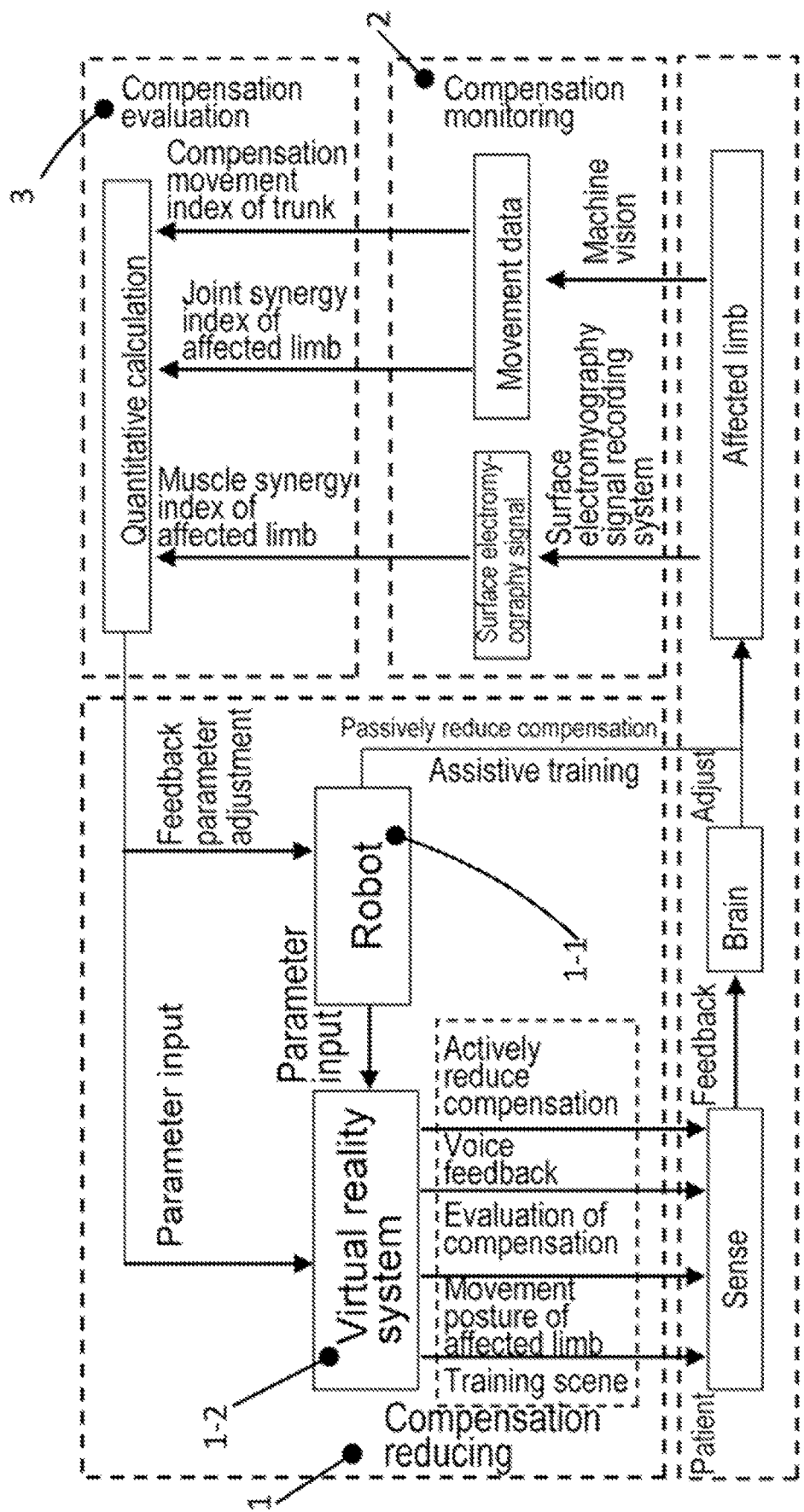

MULTIMODAL HUMAN-ROBOT INTERACTION SYSTEM FOR COMPENSATION MOVEMENT OF HEMIPLEGIC UPPER LIMB

CROSS-REFERENCE TO RELATED APPLICATION

This application is a 371 of international application of PCT application serial no. PCT/CN2019/114914, filed on Oct. 31, 2019, which claims the priority benefit of China application no. 201910272804.X, filed on Apr. 4, 2019. The entirety of each of the above mentioned patent applications is hereby incorporated by reference herein and made a part of this specification.

TECHNICAL FIELD

The present invention relates to the field of upper limb rehabilitation, in particular to a multimodal human-robot interaction system for compensation movement of a hemiplegic upper limb.

BACKGROUND

Stroke is a disease with a high fatality rate and a high disability rate. Hemiplegic upper limb dyskinesia is a common sequela of stroke, which affects the daily life of a patient severely. Rehabilitation of the hemiplegic upper limb has aroused wide public concern. High strength and large dose exercise rehabilitation plays a critical role in the recovery of the affect limb. However, as the number of patients with stroke is huge, rehabilitation therapists are in severe short. A conventional manual physical therapy cannot meet a huge rehabilitation demand. An existing upper limb rehabilitation robot can relieve the pressure of short of the rehabilitation therapists, thereby, the rehabilitation training efficiency and effect are improved and the clinical application prospect is huge. However, during the upper limb rehabilitation robot helps the hemiplegic upper limb in rehabilitation training, the patient often generates the compensation, which brings many adverse effects to the recovery of the affected limb, including dissymmetry of movement actions, reduction of stability, and even further reduction of motor function. The existing upper limb rehabilitation robot short in monitoring and evaluation mechanisms for the compensation movement of the hemiplegic upper limb, cannot feedback and improve rehabilitation training timely and cannot reduce the compensation movement effectively, such that the rehabilitation training effect of the hemiplegic upper limb is further affected.

SUMMARY

In order to overcome deficiencies in the prior art, the present invention provides a multimodal human-robot interaction system for compensation movement of a hemiplegic upper limb, which aims to solve the problem that monitoring, evaluation and reduction of the compensation movement are in short in an existing upper limb rehabilitation therapy.

The objective of the present invention is at least realized by one of the technical schemes as follows.

A multimodal human-robot interaction system for compensation movement of a hemiplegic upper limb includes a compensation movement reducing module for the hemiplegic upper limb, a compensation movement monitoring module for the hemiplegic upper limb, and a compensation movement evaluation module for the hemiplegic upper limb, wherein the compensation movement reducing module for the hemiplegic upper limb includes two portions: a robot and a virtual reality system.

Further, the robot as an executing mechanism of a training system is used for assisting the hemiplegic upper limb in performing rehabilitation training, and adjusting a training action according to a compensation monitoring result and evaluation of compensation to realize passive reducing for the compensation movement of the hemiplegic upper limb. The virtual reality system is used for displaying a rehabilitation training scene of the rehabilitation training of the hemiplegic upper limb, a real-time movement posture of the hemiplegic upper limb and the evaluation of the compensation and interacting with a patient through vision and voice to instruct the patient to reduce the compensation movement.

Further, the compensation movement monitoring module for the hemiplegic upper limb is used for recording various sensor signals and recording comprehensive data of the hemiplegic upper limb during a rehabilitation therapy in real time, the comprehensive data including a surface electromyography signal and movement data.

Further, the compensation movement evaluation module for the hemiplegic upper limb is used for quantitative calculations of three indexes of the hemiplegic upper limb, the three indexes including a muscle synergy index of an affected limb, a joint synergy index of the affected limb and a compensation movement index of a trunk.

Further, the robot is used for assisting the hemiplegic upper limb of a patient to perform hemiplegic upper limb rehabilitation training and adjusting the training action in real time to reduce the compensation movement according to a feedback parameter of the compensation movement evaluation module for the hemiplegic upper limb and transmitting training data to the virtual reality system as inputs to be displayed to the patient in real time.

Further, the compensation movement monitoring module for the hemiplegic upper limb includes a surface electromyography signal recording system and a machine vision apparatus. The surface electromyography signal recording system obtains three characteristic parameters: a root-mean-square value $$RMS(EMG) = \sqrt{\frac{\int_{t}^{t+T} EMG^2(t)dt}{T}},$$

an integrated electromyogram $iEMG = \int_{t}^{t+T}|EMG(t)|dt$ and an average power frequency $MPF = \int_{0}^{\infty} fP(f)df / \int_{0}^{\infty} P(f)df$ by extracting and analyzing the surface electromyography signal of the upper limb of the patient, wherein t is a current time, T is a width of a sampling time window, EMG (t) is a surface electromyography signal value at the current time, f is a current sampling frequency and P(f) is a surface electromyography signal power spectrum. The machine vision apparatus is used for capturing movement data of the patient, the movement data including shoulder and elbow joint movement parameters and trunk movement parameters of the hemiplegic upper limb. The shoulder and elbow joint movement parameters include an adduction/abduction angle $\theta_1$ of a shoulder joint, a flexion/extension angle $\theta_2$ of the shoulder joint, an internal and external rotation angle $\theta_3$ of the shoulder joint and a flexion and extension angle $\theta_4$ of the elbow joint. The trunk movement parameters include a front-back inclination $\theta_5$ of the trunk, a rotating angle $\theta_6$ of the trunk and a left-right inclination $\theta_7$ of the trunk.

Further, the compensation movement evaluation module for the hemiplegic upper limb performs the quantitative calculations on the muscle synergy index of the affected limb, the joint synergy index of the affected limb and the compensation movement index of the trunk respectively to obtain evaluation of the compensation movement, a score $S_1$ calculation of the muscle synergy index of the affected limb including the following steps:

(1) calculating relative deviations $E_{11}$, $E_{12}$ and $E_{13}$ of three surface electromyography signal characteristic values RMS(EMG), iEMG and MPF respectively when the patient completes same actions with an affected side and a healthy side respectively; and $$E_{11} = \frac{\text{RMS}(EMG_{\text{affected side}}) - \text{RMS}(EMG_{\text{healthy side}})}{\text{RMS}(EMG_{\text{healthy side}})} \times 100\%;$$

$$E_{12} = \frac{iEMG(\text{affected side}) - iEMG(\text{healthy side})}{iEMG(\text{healthy side})} \times 100\%;$$

$$E_{13} = \frac{MPF(\text{affected side}) - MPF(\text{healthy side})}{MPF(\text{healthy side})} \times 100\%;$$

(2) calculating the score $S_1$ of the muscle synergy index of the affected limb, wherein the larger the relative deviations of the surface electromyography signal characteristic values of the affected side and the healthy side are, the more abnormal a muscle synergy condition of the affected limb is and the lower the score $S_1$ the muscle synergy index of the affected limb is.

$$S_1 = 100 - 100 * \frac{(E_{11} + E_{12} + E_{13})}{3}.$$

Further, a calculation of a score $S_2$ of the joint synergy index of the affected limb includes the following steps:

(1) calculating relative root-mean-square errors $E_{21}$, $E_{22}$, $E_{23}$ and $E_{24}$ of the shoulder and elbow joint movement angles when the patient completes the same actions with the affected side and the healthy side respectively; and $$E_{21} = \frac{\theta_1(\text{affected side}) - \theta_1(\text{healthy side})}{\theta_1(\text{healthy side})} \times 100\%;$$

$$E_{22} = \frac{\theta_2(\text{affected side}) - \theta_2(\text{healthy side})}{\theta_2(\text{healthy side})} \times 100\%;$$

$$E_{23} = \frac{\theta_3(\text{affected side}) - \theta_3(\text{healthy side})}{\theta_3(\text{healthy side})} \times 100\%;$$

$$E_{24} = \frac{\theta_4(\text{affected side}) - \theta_4(\text{healthy side})}{\theta_4(\text{healthy side})} \times 100\%;$$

(2) calculating the score $S_2$ of the muscle synergy index of the affected limb, wherein the larger the relative deviations of the shoulder and elbow joint movement angles of the affected side and the healthy side are, the poorer a joint synergy ability of the affected limb is and the lower the score $S_2$ the joint synergy index of the affected limb is;

$$S_2 = 100 - 100 * \frac{(E_{21} + E_{22} + E_{23} + E_{24})}{4};$$

a calculation of a score $S_3$ of the compensation movement index of the trunk includes the following steps:

(1) respectively calculating relative root-mean-square errors $E_{31}$, $E_{32}$ and $E_{33}$ of the trunk movement angle during movement of the affected side and the healthy side of the patient; and $$E_{31} = \frac{\theta_5(\text{affected side}) - \theta_5(\text{healthy side})}{\theta_5(\text{healthy side})} \times 100\%;$$

$$E_{32} = \frac{\theta_6(\text{affected side}) - \theta_6(\text{healthy side})}{\theta_6(\text{healthy side})} \times 100\%;$$

$$E_{33} = \frac{\theta_7(\text{affected side}) - \theta_7(\text{healthy side})}{\theta_7(\text{healthy side})} \times 100\%;$$

(2) calculating the score $S_3$ of the compensation movement index of the trunk, the larger the relative deviation of the trunk movement angles during the movement of the affected side and the healthy side is, the more serious the compensation movement of the trunk is and the lower the score $S_3$ of the compensation movement index of the trunk is; and $$S_3 = 100 - 100 * \frac{(E_{31} + E_{32} + E_{33})}{3};$$

the evaluation S of the compensation movement of the hemiplegic upper limb is an average score of the three indexes, wherein the higher the score for evaluating the compensation movement is, the better the movement control ability of the hemiplegic upper limb is and the better the rehabilitation training effect is;

$$S=(S_1+S_2+S_3)/3.$$

Further, output data of the compensation movement evaluation module for the hemiplegic upper limb, i.e., the evaluation of the compensation movement, is input to the robot module as the feedback parameter of rehabilitation training to adjust the training action on the one hand, and is input to the virtual reality system as the quantitative index of the rehabilitation training of the hemiplegic upper limb to be displayed to the patient intuitively on the other hand, so as to instruct the patient to adjust the movement posture actively to reduce the compensation movement through visual feedback and voice feedback.

Further, the virtual reality system includes a vision display portion and a voice-interactive interface portion, input parameters thereof coming from the robot module and the compensation movement evaluation module for the hemiplegic upper limb. The virtual reality system feeds back a state of rehabilitation training of the hemiplegic upper limb to the patient in real time by displaying a virtual training scene of the rehabilitation exercise of the hemiplegic upper limb, the real-time movement posture of the affected limb and the evaluation of compensation, and instructs the patient to adjust the movement posture actively to reduce the compensation movement by combining the voice feedback.

Compared with the prior art, the present invention has the advantages and effects as follows.

The robot training system provided by the present invention can realize monitoring, evaluation and a reduction of the compensation movement in a process that the patient uses the robot for rehabilitation training, and is helpful for the patient to learn a correct movement mode, and thereby, the motor function of the hemiplegic upper limb is improved.

BRIEF DESCRIPTION OF THE DRAWINGS

FIG. 1 is a multimodal monitoring and evaluation method and reducing system for compensation movement of a hemiplegic upper limb.

In the drawing, compensation movement reducing module 1 for the hemiplegic upper limb, compensation movement monitoring module 2 for the hemiplegic upper limb, compensation movement evaluation module 3 for the hemiplegic upper limb, robot 1-1, virtual reality system 1-2.

DETAILED DESCRIPTION

Further description of specific embodiments of the present invention in detail will be made below in combination with drawings and examples, but implementation and protection of the present invention are not limited thereto. It should be noted that processes that are not described in detail particularly below are realized or understood by those skilled in the field with reference to prior art.

Examples

As shown in the FIG. 1, a multimodal human-robot interaction system for compensation movement of a hemiplegic upper limb includes a compensation movement reducing module 1 for the hemiplegic upper limb, a compensation movement monitoring module 2 for the hemiplegic upper limb, and a compensation movement evaluation module 3 for the hemiplegic upper limb, wherein the compensation movement reducing module 1 for the hemiplegic upper limb includes two portions: a robot 1-1 and a virtual reality system 1-2.

Further, the robot module 1-1 as an executing mechanism of the system is used for assisting the hemiplegic upper limb to perform rehabilitation training and to reduce the compensation movement of the hemiplegic upper limb passively according to an adjusting training action of a compensation monitoring result and an evaluation of compensation. In the example, the robot module 1-1 at least has six degrees of freedom and can use a UR5 robot of a company Universal Robots or a Roberta robot of a company ABB.

The virtual reality system 1-2 is used for displaying a rehabilitation training scene of the rehabilitation training of the hemiplegic upper limb, a real-time movement posture of the hemiplegic upper limb and the evaluation of the compensation and interacting with a patient through vision and voice to instruct the patient to reduce the compensation movement.

The compensation movement monitoring module 2 for the hemiplegic upper limb is used for recording various sensor signals and recording comprehensive data of the hemiplegic upper limb in a rehabilitation therapy in real time, the comprehensive data including a surface electromyography signal and movement data. The compensation movement monitoring module 2 for the hemiplegic upper limb includes a surface electromyography signal recording instrument and a machine vision apparatus. In the example, the surface electromyography signal recording instrument can be a TeleMyo2400 surface electromyography measuring instrument of a compound Noraxon or a Trigno Mobile portable surface electromyography testing instrument of a company DELSYS. The vision machine apparatus can be an optical movement capturing system of VICON and an optical movement capturing and analyzing system of Motion Analysis.

The surface electromyography signal recording system obtains three characteristic parameters: a root-mean-square value $$\mathrm{RMS}(EMG) = \sqrt{\frac{\int_t^{T+t} EMG^2(t)dt}{T}},$$

an integrated electromyogram $\mathrm{iEMG} = {}^{t+T}{}_t\int |\mathrm{EMG}(t)|dt$ and an average power frequency $\mathrm{MPF} = \int_0^\infty f P(f)df / \int_0^\infty P(f)df$ of the surface electromyography signal by extracting and analyzing the surface electromyography signal of the upper limb of the patient, wherein t is a current time, T is a width of a sampling time window, EMG (t) is a surface electromyography signal value at the current time, f is a current sampling frequency and P(f) is a surface electromyography signal power spectrum. The machine vision apparatus is used for capturing movement data of the patient, the movement data including shoulder and elbow joint movement parameters and trunk movement parameters of the hemiplegic upper limb. The shoulder and elbow joint movement parameters include an adduction/abduction angle $\theta_1$ of a shoulder joint, a flexion/extension angle $\theta_2$ of the shoulder joint, an internal and external rotation angle $\theta_3$ of the shoulder joint and a flexion and extension angle $\theta_4$ of the elbow joint. The trunk movement parameters include a front-back inclination $\theta_5$ of the trunk, a rotating angle $\theta_6$ of the trunk and a left-right inclination $\theta_7$ of the trunk.

The compensation movement evaluation module 3 for the hemiplegic upper limb performs Quantitative calculations on a muscle synergy index of the affected limb, a joint synergy index of the affected limb and a compensation movement index of the trunk respectively to obtain the evaluation of the compensation movement. In the example, the compensation movement evaluation module 3 for the hemiplegic upper limb can perform analysis and calculation by means of a computer system.

A calculation process of a score $S_1$ of the muscle synergy index of the affected limb includes the following steps:
(1) calculating relative deviations $E_{11}$, $E_{12}$ and $E_{13}$ of three surface electromyography signal characteristic values RMS(EMG), iEMG and MPF respectively when the patient completes same actions with an affected side and a healthy side respectively; and $$E_{11} = \frac{\mathrm{RMS}(EMG_{\mathit{affected\ side}}) - \mathrm{RMS}(EMG_{\mathit{healthy\ side}})}{\mathrm{RMS}(EMG_{\mathit{healthy\ side}})} \times 100\%;$$

$$E_{12} = \frac{iEMG\ (\text{affected side}) - iEMG\ (\text{healthy side})}{iEMG\ (\text{healthy side})} \times 100\%;$$

$$E_{13} = \frac{MPF\ (\text{affected side}) - MPF\ (\text{healthy side})}{MPF\ (\text{healthy side})} \times 100\%;$$

(2) calculating the score $S_1$ of the muscle synergy index of the affected limb, wherein the larger the relative deviations of the surface electromyography signal characteristic values of the affected side and the healthy side are, the more abnormal a muscle synergy condition of the affected limb is and the lower the score $S_1$ the muscle synergy index of the affected limb is.

$$S_1 = 100 - 100 * \frac{(E_{11} + E_{12} + E_{13})}{3};$$

A calculation process of a score $S_2$ of the joint synergy index of the affected limb includes the following steps:
(1) calculating relative root-mean-square errors $E_{21}$, $E_{22}$, $E_{23}$ and $E_{24}$ of the shoulder and elbow joint movement angles when the patient completes the same actions with the affected side and the healthy side respectively; and $$E_{21} = \frac{\theta_1 \text{ (affected side)} - \theta_1 \text{ (healthy side)}}{\theta_1 \text{ (healthy side)}} \times 100\%;$$

$$E_{22} = \frac{\theta_2 \text{ (affected side)} - \theta_2 \text{ (healthy side)}}{\theta_2 \text{ (healthy side)}} \times 100\%;$$

$$E_{23} = \frac{\theta_3 \text{ (affected side)} - \theta_3 \text{ (healthy side)}}{\theta_3 \text{ (healthy side)}} \times 100\%;$$

$$E_{24} = \frac{\theta_4 \text{ (affected side)} - \theta_4 \text{ (healthy side)}}{\theta_4 \text{ (healthy side)}} \times 100\%;$$

(2) calculating the score $S_2$ of the muscle synergy index of the affected limb, wherein the larger the relative deviations of the shoulder and elbow joint movement angles of the affected side and the healthy side are, the poorer a joint synergy ability of the affected limb is and the lower the score $S_2$ the joint synergy index of the affected limb is;

$$S_2 = 100 - 100 * \frac{(E_{21} + E_{22} + E_{23} + E_{24})}{4};$$

a calculation of a score $S_3$ of the compensation movement index of the trunk includes the following steps:
(1) respectively calculating relative root-mean-square errors $E_{31}$, $E_{32}$ and $E_{33}$ of the trunk movement angle during movement of the affected side and the healthy side of the patient; and $$E_{31} = \frac{\theta_5 \text{ (affected side)} - \theta_5 \text{ (healthy side)}}{\theta_5 \text{ (healthy side)}} \times 100\%;$$

$$E_{32} = \frac{\theta_6 \text{ (affected side)} - \theta_6 \text{ (healthy side)}}{\theta_6 \text{ (healthy side)}} \times 100\%;$$

$$E_{33} = \frac{\theta_7 \text{ (affected side)} - \theta_7 \text{ (healthy side)}}{\theta_7 \text{ (healthy side)}} \times 100\%;$$

(2) calculating the score $S_3$ of the compensation movement index of the trunk, the larger the relative deviation of the trunk movement angles in the movement of the affected side and the healthy side is, the more serious the compensation movement of the trunk is and the lower the score $S_3$ of the compensation movement index of the trunk is; and $$S_3 = 100 - 100 * \frac{(E_{31} + E_{32} + E_{33})}{3};$$

the evaluation S of the compensation movement of the hemiplegic upper limb is an average score of the three indexes, wherein the higher the score for evaluating the compensation movement is, the better the movement control ability of the hemiplegic upper limb is and the better the rehabilitation training effect is;

$$S = (S_1 + S_2 + S_3)/3.$$

The robot 1-1 is used for driving the hemiplegic upper limb of the patient to perform hemiplegic upper limb training and adjusting the training action in real time to reduce the compensation movement according to a feedback parameter of the compensation movement evaluation module 3 for the hemiplegic upper limb and transmitting training data to the virtual reality system 1-2 as an input parameter to be displayed to the patient in real time.

Output data of the compensation movement evaluation module 3 for the hemiplegic upper limb, i.e., the evaluation of the compensation movement, is input to the robot module 1-1 as the feedback parameter of rehabilitation training to adjust the training action on the one hand, and is input to the virtual reality system 1-2 as the quantitative index of the rehabilitation training of the hemiplegic upper limb to be displayed to the patient intuitively on the other hand, so as to instruct the patient to adjust the movement posture actively to reduce the compensation movement through visual feedback and voice feedback.

The virtual reality system 1-2 includes a vision display portion and a voice-interactive interface portion, input parameters thereof coming from the robot module 1-1 and the compensation movement evaluation module 3 for the hemiplegic upper limb. The virtual reality system 1-2 feeds back a state of rehabilitation training of the hemiplegic upper limb to the patient in real time by displaying a virtual training scene of the rehabilitation exercise of the hemiplegic upper limb, the real-time movement posture of the affected limb and the evaluation of the compensation, and instructs the patient to adjust the movement posture actively to reduce the compensation movement by combining the voice feedback.

A using process of the embodiment is as follows.

In a feasible example, the compensation movement reducing module 1 for the hemiplegic upper limb includes the robot 1-1 and the virtual reality system 1-2, wherein a tail end of the robot module 1-1 is connected to the hemiplegic upper limb of the patient to assist the affected limb to perform rehabilitation training, and the training data is transmitted to the virtual reality system 1-2 as the input parameter and is fed back to the patient in real time. In the process that the robot module 1-1 assists the hemiplegic upper limb to perform rehabilitation training, a surface electromyography signal recording system in the compensation movement monitoring module 2 for the hemiplegic upper limb collects the surface electromyography signal of the hemiplegic upper limb in real time to analyze and obtain the muscle synergy index of the affected limb. Meanwhile, the machine vision apparatus captures the movement data of the patient and analyzes and obtains the joint synergy index of the affected limb and the compensation movement index of the trunk; the three indexes are transmitted to the compensation movement evaluation module 3 for the hemiplegic upper limb to be analyzed and quantized to obtain the evaluation of the compensation movement of the hemiplegic upper limb. The quantitative evaluation is input to the robot module 1-1 as the feedback parameter of rehabilitation training to adjust the action of training on the one hand so as to reduce the compensation movement passively and is input to the virtual reality system 1-2 as the quantitative index of the training on the other hand to be displayed to the patient intuitively. The virtual reality system 1-2 is used for displaying a rehabilitation training scene of the rehabilitation training of the hemiplegic upper limb, a real-time movement posture of the hemiplegic upper limb and evaluation of compensation and instructing the patient to adjust the movement posture actively to reduce the compensation movement by combining the voice feedback.

The above embodiments are merely preferred embodiments of the present invention and are merely used for explaining the present invention rather than limiting the present invention. Variations, substitutions and modifications made by those skilled in the field shall fall within the scope of protection of the present invention without departing from the spirit of the present invention.

What is claimed is:

1. A multimodal human-robot interaction system for compensation movement of a hemiplegic upper limb, comprising a compensation movement reducing module for taking comprehensive data of the hemiplegic upper limb during a rehabilitation therapy in real time, a compensation movement monitoring module for the hemiplegic upper limb, and a compensation movement evaluation module for the hemiplegic upper limb, wherein the compensation movement reducing module for the hemiplegic upper limb comprising a robot and a virtual reality system; the robot is used as an executing mechanism of a training system for assisting the hemiplegic upper limb in performing rehabilitation training and adjusting a training action according to the comprehensive data of the hemiplegic upper limb during the rehabilitation therapy in real time to realize passive reducing for the compensation movement of the hemiplegic upper limb; and the virtual reality system is used for displaying a rehabilitation training scene of the rehabilitation training of the hemiplegic upper limb, a real-time movement posture of the hemiplegic upper limb and the evaluation of compensation and interacting with a patient through vision and voice to instruct the patient to reduce the compensation movement, wherein the compensation movement monitoring module for the hemiplegic upper limb comprises a surface electromyography signal recording system and a machine vision apparatus; the surface electromyography signal recording system obtains three characteristic parameters: a root-mean-square value $$RMS(EMG) = \sqrt{\frac{\int_t^{T+t} EMG^2(t)dt}{T}},$$

an integrated electromyogram $iEMG = \int_t^{t+T} |EMG(t)|dt$ and an average power frequency $MPF = \int_0^\infty fP(f)df / \int_0^\infty P(f)df$ of a surface electromyography signal by extracting and analyzing the surface electromyography signal of the upper hemiplegic limb of the patient, wherein t is a current time, T is a width of a sampling time window, EMG (t) is a surface electromyography signal value at the current time, f is a current sampling frequency and P(f) is a surface electromyography signal power spectrum; the machine vision apparatus is used for capturing movement data of the patient, the movement data comprising shoulder and elbow joint movement parameters and trunk movement parameters of the hemiplegic upper limb; the shoulder and elbow joint movement parameters comprise an adduction/abduction angle $\theta_1$ of a shoulder joint, a flexion/extension angle $\theta_2$ of the shoulder joint, an internal and external rotation angle $\theta_3$ of the shoulder joint and a flexion and extension angle $\theta_4$ of the elbow joint; and the trunk movement parameters comprise a front-back inclination $\theta_5$ of the trunk of the patient, a rotating angle $\theta_6$ of the trunk of the patient and a left-right inclination $\theta_7$ of the trunk of the patient.

2. The multimodal human-robot interaction system for the compensation movement of the hemiplegic upper limb according to claim 1, wherein the compensation movement monitoring module for the hemiplegic upper limb, which comprises the surface electromyography signal recording system and the machine vision apparatus, is used for taking the comprehensive data of the hemiplegic upper limb during the rehabilitation therapy in real time, the comprehensive data comprising a surface electromyography signal taken by the surface electromyography signal recording system and movement data taken by the machine vision apparatus.

3. The multimodal human-robot interaction system for the compensation movement of the hemiplegic upper limb according to claim 1, wherein the compensation movement evaluation module for the hemiplegic upper limb is used for quantitative calculations of three indexes of the hemiplegic upper limb, the three indexes comprising a muscle synergy index of an affected limb, a joint synergy index of the affected limb and a compensation movement index of a trunk of the patient.

4. The multimodal human-robot interaction system for the compensation movement of the hemiplegic upper limb according to claim 1, wherein the robot is used for driving the hemiplegic upper limb of the patient to perform hemiplegic upper limb rehabilitation training and adjusting the training action in real time to reduce the compensation movement according to a feedback parameter of the compensation movement evaluation module for the hemiplegic upper limb and transmitting training data to the virtual reality system as an input parameter to be displayed to the patient in real time.

5. The multimodal human-robot interaction system for the compensation movement of the hemiplegic upper limb according to claim 3, wherein the compensation movement evaluation module for the hemiplegic upper limb performs the quantitative calculations on the muscle synergy index of the affected limb, the joint synergy index of the affected limb and the compensation movement index of the trunk of the patient respectively to obtain an evaluation of the compensation movement, a score $S_1$ calculation of the muscle synergy index of the affected limb comprising the following steps:

(1) calculating relative deviations $E_{11}$, $E_{12}$ and $E_{13}$ of the three characteristic parameters RMS(EMG), iEMG and MPF respectively when the patient completes an action with an affected side of; and $$E_{11} = \frac{RMS(EMG_{affected\ side}) - RMS(EMG_{healthy\ side})}{RMS(EMG_{healthy\ side})} \times 100\%;$$

$$E_{12} = \frac{iEMG\ (affected\ side) - iEMG\ (healthy\ side)}{iEMG\ (healthy\ side)} \times 100\%;$$

$$E_{13} = \frac{MPF\ (affected\ side) - MPF\ (healthy\ side)}{MPF\ (healthy\ side)} \times 100\%;$$

(2) calculating the score $S_1$ of the muscle synergy index of the affected limb, wherein the larger the relative deviations of the surface electromyography signal characteristic values of the affected side and the healthy side are, the more abnormal a muscle synergy condition of the affected limb is compared with a muscle synergy condition of a healthy limb, and the lower the score $S_1$ the muscle synergy index of the affected limb is compared with a muscle synergy index of a healthy limb:

$$S_1 = 100 - 100 * \frac{(E_{11} + E_{12} + E_{13})}{3};$$

6. The multimodal human-robot interaction system for the compensation movement of the hemiplegic upper limb according to claim 5, wherein a calculation process of a score $S_2$ of the joint synergy index of the affected limb comprises the following steps:
   (1) calculating relative root-mean-square errors $E_{21}$, $E_{22}$, $E_{23}$ and $E_{24}$ of the shoulder and elbow joint movement angles when the patient completes an action with the affected side of the patient and a same action with the healthy side of the patient respectively; and $$E_{21} = \frac{\theta_1 \text{ (affected side)} - \theta_1 \text{ (healthy side)}}{\theta_1 \text{ (healthy side)}} \times 100\%;$$

$$E_{22} = \frac{\theta_2 \text{ (affected side)} - \theta_2 \text{ (healthy side)}}{\theta_2 \text{ (healthy side)}} \times 100\%;$$

$$E_{23} = \frac{\theta_3 \text{ (affected side)} - \theta_3 \text{ (healthy side)}}{\theta_3 \text{ (healthy side)}} \times 100\%;$$

$$E_{24} = \frac{\theta_4 \text{ (affected side)} - \theta_4 \text{ (healthy side)}}{\theta_4 \text{ (healthy side)}} \times 100\%;$$

(2) calculating the score $S_2$ of the muscle synergy index of the affected limb, wherein the larger the relative deviations of the shoulder and elbow joint movement angles of the affected side and the healthy side are, the poorer a joint synergy ability of the affected limb is compared with a joint synergy ability of a healthy limb and the lower the score $S_2$ the joint synergy index of the affected limb is compared with a joint synergy index of the healthy limb;

$$S_2 = 100 - 100 * \frac{(E_{21} + E_{22} + E_{23} + E_{24})}{4};$$

a calculation of a score $S_3$ of the trunk compensation movement index comprises the following steps:
   (1) respectively calculating relative root-mean-square errors $E_{31}$, $E_{32}$ and $E_{33}$ of the trunk movement angle during movement of the affected side and the healthy side of the patient; and $$E_{31} = \frac{\theta_5 \text{ (affected side)} - \theta_5 \text{ (healthy side)}}{\theta_5 \text{ (healthy side)}} \times 100\%;$$

$$E_{32} = \frac{\theta_6 \text{ (affected side)} - \theta_6 \text{ (healthy side)}}{\theta_6 \text{ (healthy side)}} \times 100\%;$$

$$E_{33} = \frac{\theta_7 \text{ (affected side)} - \theta_7 \text{ (healthy side)}}{\theta_7 \text{ (healthy side)}} \times 100\%;$$

(2) calculating the score $S_3$ of the trunk compensation movement index, the larger the relative deviation of the trunk movement angles during the movement of the affected side and the healthy side is, the more serious the compensation movement of the trunk of the affected side is compared with a compensation movement of the trunk of the healthy side, and the lower the score $S_3$ of the trunk compensation movement index of the affected side is compared with a trunk compensation movement index of the healthy side; and $$S_3 = 100 - 100 * \frac{(E_{31} + E_{32} + E_{33})}{3};$$

the evaluation S of the compensation movement of the hemiplegic upper limb is an average score of the three indexes, wherein the higher the score for evaluating the compensation movement is, the better the movement control ability of the hemiplegic upper limb is and the better the rehabilitation training effect is:

$S=(S_1+S_2+S_3)/3$.

7. The multimodal human-robot interaction system for the compensation movement of the hemiplegic upper limb according to claim 1, wherein output data of the compensation movement evaluation module for the hemiplegic upper limb, which is a evaluation of the compensation movement, is input to a robot module as a feedback parameter of rehabilitation exercise to adjust the training action, and is input to the virtual reality system as an quantitative index of a rehabilitation training condition of the hemiplegic upper limb to be displayed to the patient intuitively, so as to instruct the patient to adjust the movement posture actively to reduce the compensation movement through the vision and the voice.

8. The multimodal human-robot interaction system for the compensation movement of the hemiplegic upper limb according to claim 1, wherein the virtual reality system comprises a display and a speaker, input parameters thereof coming from a robot module and the compensation movement evaluation module for the hemiplegic upper limb; the virtual reality system feeds back a state of rehabilitation training of the hemiplegic upper limb to the patient in real time by displaying the rehabilitation training scene of a rehabilitation exercise of the hemiplegic upper limb, the real-time movement posture of an affected limb and the evaluation of compensation, and instructs the patient to adjust a movement posture actively to reduce the compensation movement by providing a voice feedback.

* * * * *